(12) United States Patent
Godfrey, Jr. et al.

(10) Patent No.: US 8,808,156 B1
(45) Date of Patent: Aug. 19, 2014

(54) MINIMALLY INVASIVE APPLICATOR FOR INTRAOPERATIVE RADIOTHERAPY

(76) Inventors: Loren Godfrey, Jr., Kinnelon, NJ (US); Loren Godfrey, Sr., Farmington, CT (US)

( * ) Notice: Subject to any disclaimer, the term of this patent is extended or adjusted under 35 U.S.C. 154(b) by 641 days.

(21) Appl. No.: 13/102,050

(22) Filed: May 5, 2011

Related U.S. Application Data

(63) Continuation-in-part of application No. 12/416,677, filed on Apr. 1, 2009.

(60) Provisional application No. 61/331,689, filed on May 5, 2010.

(51) Int. Cl.
*A61N 5/00* (2006.01)
*A61N 5/10* (2006.01)

(52) U.S. Cl.
CPC ....... *A61N 5/1007* (2013.01); *A61N 2005/1012* (2013.01)
USPC .................................. 600/3; 604/57; 604/116

(58) Field of Classification Search
USPC ................ 600/1–8; 248/67.7, 68.1, 74.1, 248/596–598, 912; 604/21, 57, 116
See application file for complete search history.

(56) References Cited

U.S. PATENT DOCUMENTS 3,060,924 A * 10/1962 Rush ................................ 600/6
4,331,131 A * 5/1982 Kumar ............................. 600/6

* cited by examiner

*Primary Examiner* — Charles A Marmor, II
*Assistant Examiner* — Carrie R Dorna
(74) *Attorney, Agent, or Firm* — Michael D. Eisenberg

(57) ABSTRACT

The present invention relates to an applicator for delivering any of a plurality of predetermined radiation fields to a target in intraoperative radiotherapy. In a variant, the applicator comprises: a panel and at least one first pair of first and second grippers pivotally connected to the panel with each gripper having loop on an end. The loop is connected to an arm and the arm pivotally attached to the panel. The first and second grippers are configured to rotate in opposite directions to form an open position and come to a stopping point. The loops of the grippers are configured to slide under one another while rotating into a retracted configuration. Two end units are disposed on opposite ends of the panel, configured for being grasped by two independent graspers for fixing the applicator in position.

10 Claims, 2 Drawing Sheets

MINIMALLY INVASIVE APPLICATOR FOR INTRAOPERATIVE RADIOTHERAPY

CROSS-REFERENCES TO RELATED APPLICATIONS

The present application claims priority from U.S. Provisional Application Ser. No. 61/331,689 filed on May 5, 2010, and is a continuation in part of U.S. application Ser. No. 12/416,677 filed Apr. 1, 2009 which are hereby incorporated herein by reference in the respective entirety of each.

TECHNICAL FIELD

The present invention, in some embodiments thereof, relates to minimally invasive applicators for robotic-assisted and non-robotic assisted intraoperative radiotherapy.

BACKGROUND OF THE INVENTION

Radiation therapy has a long history of providing increased local and regional control of disease when used after surgery for malignancies of the brain, head & neck, lung, breast, stomach, pancreas, colon, rectum, uterus, cervix, prostate, skin, esophagus, kidney, bladder, ovary and soft tissues (sarcomas). Intraoperative radiotherapy (IORT) is a subspecialty in which the radiotherapy is given at the time of surgery. Its primary advantage is the ability to surgically remove organs-at-risk from the post-operative field during treatment, enabling higher doses to be given safely. IORT has been in use for many years at specialized facilities and has a wealth of clinical data to support its safety and efficacy.

Two concomitant developments have created an opportunity to overcome the current limitations of IORT. One is the development of electronic brachytherapy. A catheter-based radiotherapy system that produces ionizing radiotherapy from a very small source. It can effectively achieve desired radiotherapy fields that were previously created with seed-sized isotopes. Its treatment energy is low enough that expensive shielding is not required, and as it is not radioactive (when the machine is off), expensive procedures and protections are not required.

The second development is surgical robotics. A success story developing over the previous decade, surgical robots have facilitated more and more minimally invasive procedures, including oncologic resections. The rapid recovery time and shortened hospital stays have been well-received in all applications. Prostatectomies and hysterectomies comprise the majority of oncologic surgeries, though this is evolving. Patients are evaluated for post-operative radiotherapy in the same manner after either a robotic or traditional resection.

Applicators for manipulating radiation delivery catheters or seed-sized isotopes have been developed for use in IORT in a very precise, controlled and "real time" environment. Such applicators need to be very stable and not vulnerable to perturbations while being manipulated in the operative theater.

Treatment of irregular surfaces, anticipated to be a common condition for treatment, requires careful planning and precise localization of the applicator to cover a target surface of a tissue with a uniform dose distribution. Prior to treatment, precise measurements are obtained to determine the distance from each source position within the applicator to the intended target surface. A map of the irregular surface is thus rendered, and a treatment plan is calculated with this data. No movement of the applicator is permitted between when the measurements are obtained and when the treatment is given, a period of time that may last between 15-30 minutes.

It would therefore be advantageous to have a minimally invasive applicator which can be firmly secured in a durable, immobile position for both planning and treatment.

BRIEF SUMMARY OF EMBODIMENTS OF THE INVENTION

The present invention relates to an applicator for delivering any of a plurality of predetermined radiation fields to a target in intraoperative radiotherapy.

In a variant, the applicator comprises: a panel and at least one first pair of first and second grippers pivotally connected to the panel with each gripper having loop on an end. The loop is connected to an arm and the arm pivotally attached to the panel. The first and second grippers are configured to rotate in opposite directions to form an open position and come to a stopping point. The loops of the grippers are configured to slide under one another while rotating into a retracted configuration. Two end units are disposed on opposite ends of the panel, configured for being grasped by two independent graspers for fixing the applicator in position.

In another variant of the applicator, the two end units are spherical.

In a further variant of the applicator, a second pair of grippers are pivotally connected to an opposite side of the panel relative to the first pair of grippers. Each gripper has a loop on an end configured to receive a catheter. The loop is connected to an arm and the arm is pivotally attached to the panel. The first and second grippers are configured to rotate in opposite directions to form an open position and come to a stopping point, and the loops of the grippers are configured to slide under one another when rotating into a retracted configuration.

In yet another variant of the applicator, the grippers are joined to the panel by respective pegs that are connected to a spring mechanism. The spring mechanism is configured such that when wound, the grippers are pulled toward the spring mechanism and retracted onto the surface of the panel, and n when the spring mechanism is released, the grippers are rotated about their respective pegs into an open configuration.

In still a further variant of the applicator, each pair of grippers are connected to a single spring mechanism.

In another variant of the applicator, the panel has through holes for receiving radiation sources, and the holes align with the loops of the gripper when retracted.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles.

Although the accompanying descriptive text may refer to such views as "top," "bottom" or "side" views, such references are merely descriptive and do not imply or require that the invention be implemented or used in a particular spatial orientation unless explicitly stated otherwise.

Figure 1A:
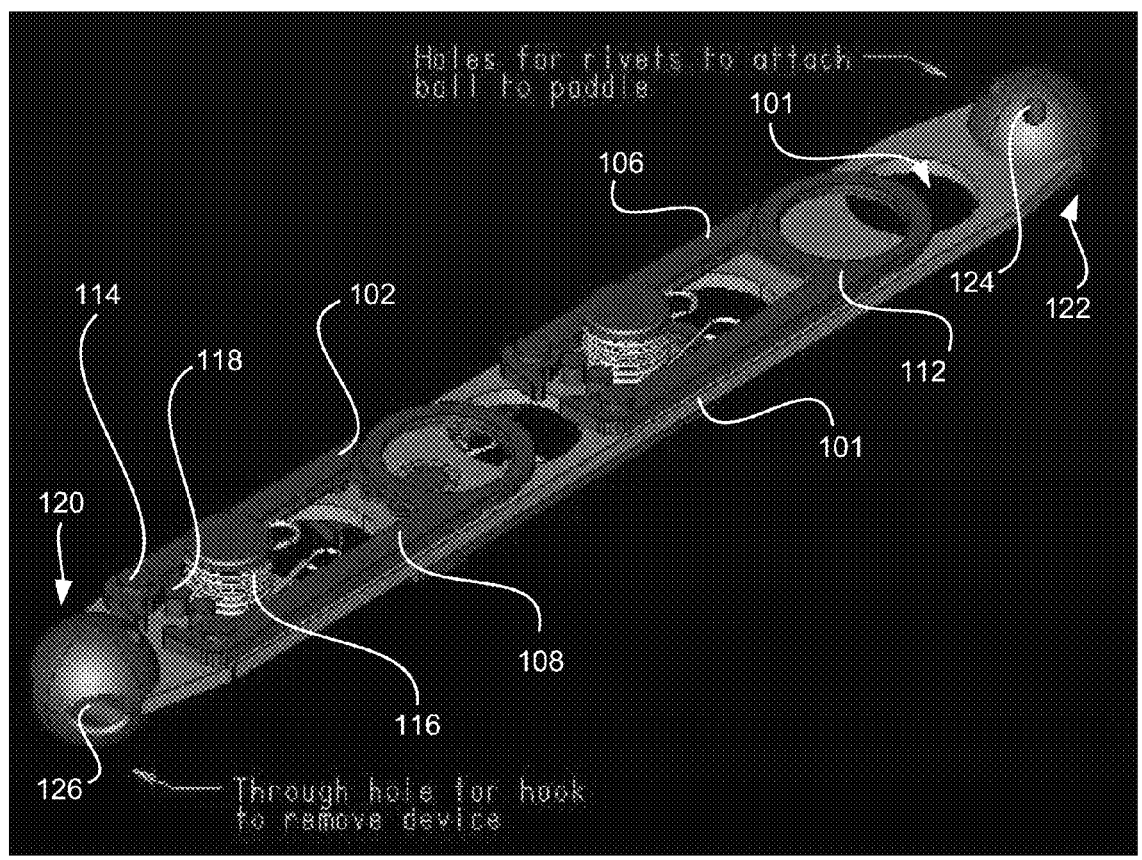
Figure 16:
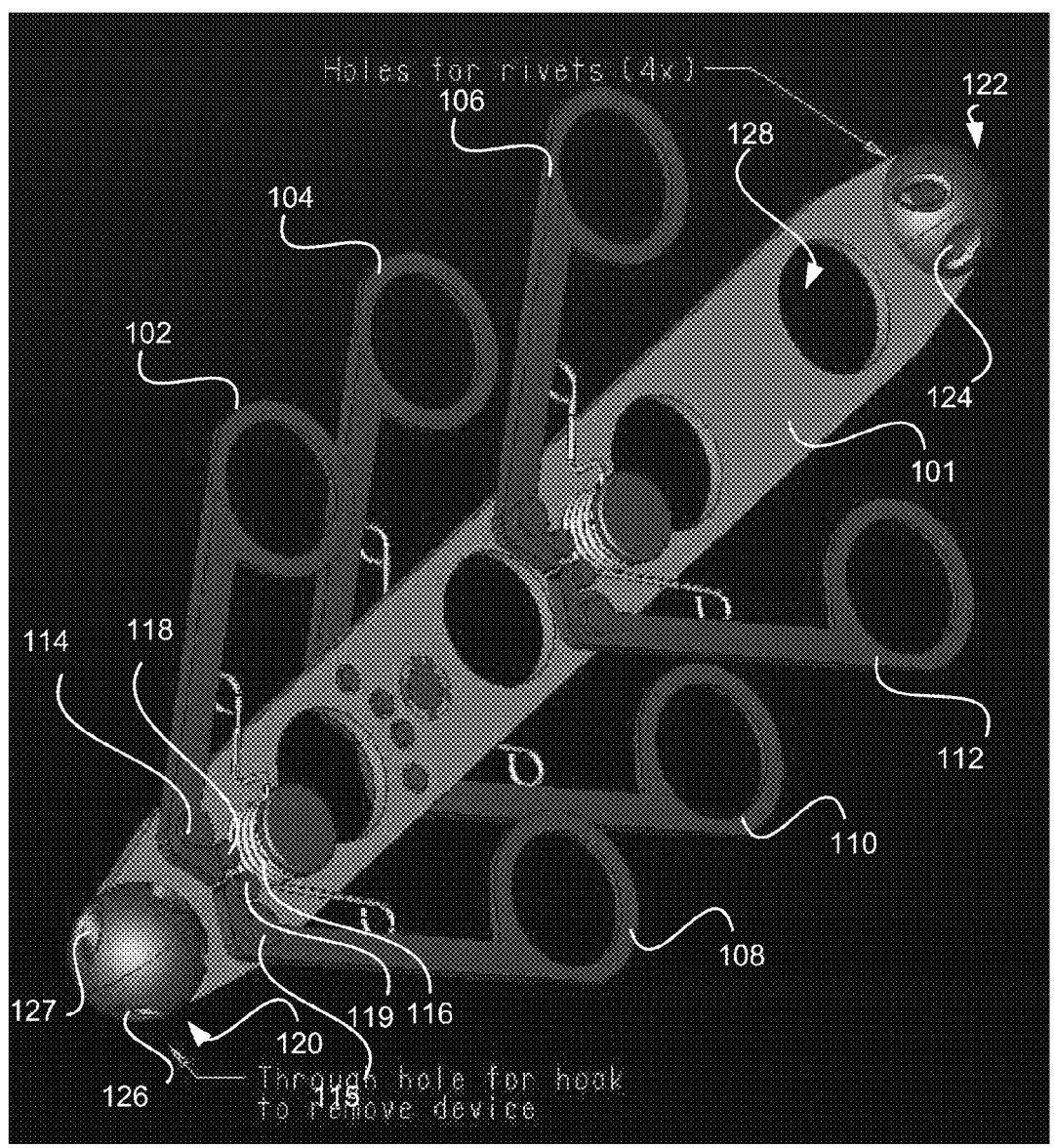

FIGS. 1a-1b are drawings illustrating an applicator for delivering a radiation source close to a target tissue, according to some embodiments of the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring now to the figures, FIGS. 1a-1b are drawings illustrating an applicator 100 for delivering a radiation source close to a target tissue, according to some embodiments of the present invention. In FIG. 1a, the applicator 100 is shown in a closed configuration thereof. In FIG. 1b, the applicator 100 is shown in an open configuration thereof.

The applicator 100 includes an oblong flat panel 101 for supporting all the elements of the applicator 100. The applicator includes a left sphere 120 and a right sphere 122, the spheres 120 and 122 being located at opposite ends of the panel 101. In a variant, the spheres have a diameter measuring about 6 millimeters. Each sphere sports four holes, like the hole 124, for receiving the rivets of a grasper. Two holes are in the half sphere below the plane of the panel 101 and two holes are in the half sphere above the plane of the panel 101. The dimensions and locations of the holes on the spheres are chosen according to the dimensions of a grasper, so that each sphere tightly grasped by an independent grasper to secure the applicator 100 at two points. In a variant, the graspers are joined to robotic arms. In another variant, the graspers are DaVinci Prograspers. Securing the applicator 100 at two points stabilizes the applicator 100 and ensures that the applicator 100 does not move when the measurements are taken and when the treatment is given.

At least one of the spheres further includes a channel, such as the channel having an entrance at the hole 126 and an exit at the hole 127 on the sphere 120. The channel is designed for being traversed by a hook attached to a long thin shaft for introducing the applicator 100 into a patient's body and for withdrawing the applicator 100 out of the patient's body. In a variant, the shaft has a length of about 15 centimeters and a diameter of about 5 millimeters, and is designed for being inserted through a minimally invasive abdominopelvic wall incision. In another variant, the diameter of the channes is about 2 millimeters.

According to some embodiments of the present invention, the applicator 100 comprises six catheter grippers (102, 104, 106, 108, 110, and 112), for holding the catheters containing the radiation sources at predetermined positions with respect to the target. The grippers are set in pairs, each pair being joined to a spring mechanism. When the spring mechanism is wound, the grippers are retracted onto the surface of the board 101, decreasing the surface area of the applicator 100. This mode will hereafter be called "closed mode", and is shown in FIG. 1a. In the closed mode, the applicator 100 is inserted into and withdrawn from the body of the patient via an incision. According to some embodiments of the present invention, in the closed mode, the applicator 100 has a length of about 70 millimeters and a width of about 8 millimeters. When the spring mechanism is released, each gripper rotates about a peg, out of the surface of the board 101, as shown in FIG. 1b. This mode will hereafter be called "open mode". After being inserted into the patient's body in the closed mode, the applicator is released into the open mode, and one or more catheters are inserted into the grippers.

To explain the open mode and closed mode, we refer FIGS. 1a-1b. The gripper 102 is joined to the panel or board 101 via the peg 114, and is joined to the spring mechanism 116. The gripper 108 is also joined to the spring mechanism 116. When the spring mechanism 116 is wound, the grippers 102 and 108 are pulled toward the spring mechanism 116 and retracted onto the surface of the board 101, as shown in FIG. 1a. In FIG. 1b, the spring mechanism 116 is released, and the gripper 102 is rotated counterclockwise about the peg 114. Similarly, the gripper 108 is rotate clockwise about the peg 115. The rotation of the gripper 102 stops when a section of the gripper 102 reaches a stopping pin 118, setting the gripper 102 at a predetermined distance from the board 101. Similarly, the gripper 108 is set into its predetermined position when a section of the gripper 108 reaches a stopping pin 119.

According to some embodiments of the present invention, the board 101 sports one or more openings, such as the opening 128, for holding one or more catheters containing the radiation sources.

In order to decrease the number of incisions made, the applicator 100 is first introduced into the patient's body via a first incision, by using the hook and shaft described above. The applicator 100 is disengaged from the hook and shaft by sliding the hook out of the first incision. The shaft and hook are then withdrawn from the operative field. The applicator 100 is then grasped on the left sphere 120 by the DaVinci prograsper, which has been inserted into the patience body via one of the four incisions required by the DaVinci robot. The applicator 100 is manipulated into a desirable position, generally directly above or in close proximity to the target. A second DaVinci prograsper inserted through another one of the incisions required by the DaVinci robot then secures the right sphere 122 to maintain immobility at two secure points. At this point, the target is ready for treatment planning, and the port through which the applicator was introduced is available for use, for delivering one or more catheters containing the radiation source. In a previous rendering, two separate incisions were required: one for the introduction of the applicator and one for the introduction of the catheters.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An applicator for delivering any of a plurality of predetermined radiation fields to a target in intraoperative radiotherapy, the applicator comprising:
    a panel;
    at least one first pair of first and second grippers pivotally connected to the panel, each gripper having a loop on an end configured to receive a catheter, the loop connected to an arm and the arm pivotally attached to the panel, wherein the first and second grippers are configured to rotate in opposite directions to form an open position and come to a stopping point, and wherein the loops of the grippers are configured to slide under one another while rotating into a retracted configuration;
    two end units disposed on opposite ends of the panel, configured for being grasped by two independent graspers for fixing the applicator in position; and
    a second pair of grippers pivotally connected to an opposing side of the panel relative the first pair of grippers, each gripper having a loop on an end, the loop connected to an arm and the arm pivotally attached to the panel, wherein the first and second grippers are configured to rotate in opposite directions from an open position and come to a stopping point, and wherein the loops of the grippers are configured to slide under one another when in a retracted configuration.

2. The applicator of claim 1, wherein the two end units are spherical.

3. The applicator of claim 1, wherein each pair of grippers is joined to the panel by a respective peg that is connected to a spring mechanism, wherein the spring mechanism is configured such that when wound, grippers of the first and second pairs are pulled toward the spring mechanism and retracted onto the surface of the panel, and wherein when the spring mechanism is released, the grippers of each pair are rotated about their respective pegs into an open configuration.

4. The applicator of claim 1, wherein each pair of grippers is connected to a single spring mechanism.

5. The applicator of claim 1, wherein the panel comprises through holes for receiving radiation sources, that align with the loops of the gripper of each pair when retracted.

6. An applicator for delivering any of a plurality of predetermined radiation fields to a target in intraoperative radiotherapy, the applicator comprising:
   a panel;
   at least one first pair of first and second grippers pivotally connected to the panel, each gripper having a loop on an end configured to receive a catheter, the loop connected to an arm and the arm pivotally attached to the panel, wherein the first and second grippers are configured to rotate in opposite directions to form an open position and come to a stopping point, and wherein the loops of the grippers are configured to slide under one another while rotating into a retracted configuration;
   two end units disposed on opposite ends of the panel, configured for being grasped by two independent graspers for fixing the applicator in position;
   wherein grippers of the at least one first pair are joined to the panel by a peg that is connected to a spring mechanism, wherein the spring mechanism is configured such that when wound, the grippers of the at least one first pair are pulled toward the spring mechanism and retracted onto the surface of the panel, and wherein when the spring mechanism is released, the grippers of the at least one first pair are rotated about their peg into an open configuration.

7. The applicator of claim 6, wherein the two end units are spherical.

8. The applicator of claim 6, further comprising a second pair of grippers pivotally connected to an opposite side of the panel relative to the first pair of grippers, each gripper having a loop on an end, the loop connected to an arm and the arm pivotally attached to the panel, wherein the first and second grippers are configured to rotate in opposite directions from an open position and come to a stopping point, and wherein the loops of the grippers are configured to slide under one another when in a retracted configuration.

9. The applicator of claim 6, wherein each pair of grippers is connected to a single spring mechanism.

10. The applicator of claim 6, wherein the panel comprises at least one through holes for receiving a radiation source, that aligns with the loops of the grippers of the at least one pair when retracted.

* * * * *